United States Patent [19]    [11]    4,287,375
Möller et al.    [45]    Sep. 1, 1981

[54] PROCESS OF CONVERTING ETHYLBENZENE TO STYRENE BY CATALYTIC DEHYDROGENATION

[75] Inventors: Friedrich-Wilhelm Möller, Friedrichsdorf; Henning Buchold, Maintal; Helmut Klein, Hanau; Otto-Ludwig Garkisch, Bad Soden; Friedrich Gütlhuber, Metten; Walter Laber, Deggendorf, all of Fed. Rep. of Germany

[73] Assignee: Metallgesellschaft Aktiengesellschaft, Frankfurt, Fed. Rep. of Germany

[21] Appl. No.: 129,460

[22] Filed: Mar. 11, 1980

[30] Foreign Application Priority Data

Mar. 13, 1979 [DE] Fed. Rep. of Germany ....... 2909763

[51] Int. Cl.$^3$ ............................................. C07C 5/333
[52] U.S. Cl. .................................. 585/440; 585/442; 585/444; 585/445
[58] Field of Search ................ 585/440, 445, 444, 442

[56] References Cited

U.S. PATENT DOCUMENTS

| | | | |
|---|---|---|---|
| 2,374,826 | 5/1945 | Mayland | 585/445 |
| 3,100,807 | 8/1963 | Hatfield et al. | 585/440 |
| 3,158,564 | 11/1964 | Cole | 585/440 |
| 3,702,346 | 11/1972 | Kellar | 585/440 |
| 3,807,963 | 4/1974 | Smith | 585/924 |
| 4,049,579 | 9/1977 | Manning | 585/440 |

Primary Examiner—Delbert E. Gantz
Assistant Examiner—Joseph A. Boska
Attorney, Agent, or Firm—Sprung, Felfe, Horn, Lynch & Kramer

[57] ABSTRACT

The invention relates to a process of converting ethylbenzene to styrene by catalytic dehydrogenation at temperatures of about 600° C. in the presence of water vapor in a tubular reactor. The heat required for the dehydrogenation is fed to the tubular reactor with a molten salt bath. The dehydrogenation is effected isothermally and in a single stage under atmospheric pressure or preferable under a subatmospheric pressure with a water vapor-ethylbenzene ratio of 1.2 to 1.5 kg of water vapor per kg of ethylbenzene. The temperature of the ethylbenzene-water-vapor mixture entering the tubular reactor is maintained 50° to 100° C. below the temperature of the molten salt bath.

3 Claims, No Drawings

PROCESS OF CONVERTING ETHYLBENZENE TO STYRENE BY CATALYTIC DEHYDROGENATION

BACKGROUND OF THE INVENTION

1. Field of the Invention

This invention relates to a process of converting ethylbenzene to styrene by catalytic dehydrogenation at temperatures of about 600° C. in the presence of water vapor in a tubular reactor.

2. Discussion of the Prior Art

It is known to convert ethyl benzene to styrene by catalytic dehydrogenation in the presence of water vapor at temperatures of 560° to about 600° C. In the processes which have been commercially adopted and are carried out in a gas-fired tubular reactor or in an adiabatic shaft furnace reactor or in an annular cracking reactor, an economically satisfactory conversion can be effected only in conjunction with poor selectivities and high steam supply rates.

In a gas-fired tubular reactor, a conversion of about 40 mole percent is usually achieved. Apart from the low conversion, that process has the disadvantage that it involves a high heat consumption caused by the circulation of hot gases in large quantities, so that energy is required at a high rate, and that the hot gas entering the tubular reactor must be at a high temperature of about 700° C.

It is also known to convert ethylbenzene to styrene by adiabatic dehydrogenation. In that case the heat required for the reaction must be supplied by a feeding of hot water vapor at a high rate. To effect an economically satisfactory conversion, the dehydrogenation is effected in two stages and the mixed reactants must be reheated before entering the second reactor. In that process the temperature of the mixture must not rise substantially above 630° C. because the ethylbenzene may otherwise be cracked. On the other hand, the temperature must not decrease below 565° C. because the reaction rate would otherwise decrease strongly (Chemi-Ing.Techn. 37, No. 4 (1965), pp. 361-367).

A disadvantage of that process resides in that more water vapor is required than in the process using a tubular reactor. For instance, if preheating is effected to a temperature of 500° C., about 2.3 kg of water vapor at a temperature of about 710° C. and a pressure of about 7 to 10 bars will be required per kg of ethylbenzene. Besides, as a result of the cracking reactions the yield of styrene is lower than where a tubular reactor is used. Another disadvantage resides in that the reaction product obtained by the adiabatic process contains twice as much water vapor so that larger cooling means are required for the condensation.

SUMMARY OF THE INVENTION

It is an object of the invention to avoid these and other disadvantages inherent in the state of the art and to provide a process which combines a high conversion and high selectivity and can be carried out with a great saving of energy.

This object is accomplished according to the invention in that heat at the rate required for the dehydrogenation is supplied to the tubular reactor with a molten salt bath, the dehydrogenation is effected isothermally in a single stage under atmospheric pressure or preferably under a subatmospheric pressure and with a water vapor-ethylbenzene ratio of 1.2 to 1.5 kg of steam per kg of ethylbenzene, and the temperature of the ethylbenzene-water vapor mixture entering the tubular reactor is 50° to 100° C. below the temperature of the molten salt bath.

In accordance with the invention the molten salt bath consists essentially of a mixture of sodium carbonate, potassium carbonate and lithium carbonate. The preferred composition of the molten salt bath used is a mixture of 30% by weight sodium carbonate, 30% by weight lithium carbonate and 40% by weight potassium carbonate.

To special advantage, the dehydrogenation is effected within the scope of the invention under an absolute pressure of 0.3 to 1.0 bar.

In accordance with a preferred further feature of the invention the temperature difference between the temperature of the molten salt bath and the reaction temperature is less that 20° C.

The advantages afforded by the invention reside particularly in that ethylbenzene can be converted to styrene by a simple and economical dehydrogenating process. The process can be carried out with a high selectivity and result in a yield of styrene which is much higher than in the prior art. The use of water vapor only at low rate means in a substantial saving of energy. Because a cracking of the ethylbenzene is substantially avoided, the resulting reaction product contains only small amounts of byproducts and for this reason has a very high purity.

The invention will be described with reference to the following examples.

EXAMPLES

A tubular reactor having a tube which has a length of 3000 mm and is 40 mm in diameter and is provided with a molten salt bath heating system according to the invention was charged with 3 liters of a commercially available dehydrogenation catalyst.

Ethylbenzene at a rate of 2.6 kg/h was evaporated and mixed with steam at a rate of 3.25 kg/h. The mixture was preheated at 530° C. The resulting reaction mixture was contacted with the catalyst under various pressures of 1.4 bars and 1.0 to 0.6 bar and at a salt bath temperature of 610° C. The reaction product was cooled and subsequently condensed to recover water and the liquid organic products stated hereinafter. The analysis of said organic phase by gas chromatography revealed the following composition:

|  | 1.4 bars | 1.0 bar | 0.6 bar |
|---|---|---|---|
| Organic liquid phase, kg/h | 2.56 | 2.55 | 2.55 |
| Ethylbenzene, % by weight | 49.2 | 39.86 | 35.16 |
| Styrene, % by weight | 49.0 | 57.66 | 62.02 |
| Benzene, % by weight | 0.3 | 0.32 | 0.41 |
| Toluene, % by weight | 1.3 | 1.76 | 2.02 |
| High-boiling compounds, % by weight | 0.2 | 0.40 | 0.39 |

The following conversion from ethylbenzene to styrene was measured:

| Conversion, mole percent | 51.6 | 60.8 | 65.5 |
|---|---|---|---|
| and the corresponding Selectivity | 95.3 | 95.0 | 94.7 |

During the tests, dehydrogenated gas was produced at a measured rate of 297 standard liters per hour. This gas had the following composition:

| $CO_2$, | % by volume | 7.8 | 6.4 | 6.2 |
|---|---|---|---|---|
| CO | " | 0.5 | 0.23 | 0.2 |
| $H_2$ | " | 90.8 | 92.97 | 93.2 |
| $CH_4$ | " | 0.9 | 0.4 | 0.4 |

What is claimed is:

1. In a process of converting ethylbenzene to styrene by catalytic dehydrogenation at a temperature about 600° C. in the presence of water vapor in a tubular reactor, the improvement which comprises supplying heat to said tubular reactor in the form of a molten salt bath, consisting essentially of a mixture of sodium carbonate, potassium carbonate and lithium carbonate, effecting dehydrogenation isothermally in said tubular reactor in a single stage under atmospheric pressure or under a subatmospheric pressure and with a water vapor-ethylbenzene ratio of 1.2–1.5 kg steam per kg ethylbenzene, the temperature of the ethylbenzene/water vapor mixture introduced into the tubular reactor being 50° to 100° C. below the temperature of the molten salt bath.

2. A process according to claim 1, wherein the dehydrogenation is effected under an absolute pressure of 0.3 to 1.0 bars.

3. A process according to claim 1, wherein the temperature difference between the temperature of the molten salt bath and the reaction temperature is kept below 20° C.

* * * * *